(12) United States Patent
Kollewe

(10) Patent No.: US 8,466,393 B2
(45) Date of Patent: Jun. 18, 2013

(54) DEVICE FOR TEMPERING A TEST FLUID

(76) Inventor: Thomas Kollewe, Hamburg (DE)

( * ) Notice: Subject to any disclaimer, the term of this patent is extended or adjusted under 35 U.S.C. 154(b) by 793 days.

(21) Appl. No.: 12/623,715

(22) Filed: Nov. 23, 2009

(65) Prior Publication Data

US 2010/0314383 A1 Dec. 16, 2010

(30) Foreign Application Priority Data

Jun. 10, 2009 (DE) .................... 20 2009 008 270 U

(51) Int. Cl.
H01L 29/72 (2006.01)
(52) U.S. Cl.
USPC ................. 219/600; 219/121.39; 219/667
(58) Field of Classification Search
USPC .................... 219/121.39, 600, 667
See application file for complete search history.

(56) References Cited

U.S. PATENT DOCUMENTS

| 5,232,667 A | 8/1993 | Hieb et al. |
| 5,656,106 A * | 8/1997 | Amateau et al. ............ 148/586 |
| 2003/0121894 A1 * | 7/2003 | Sanders et al. .......... 219/121.39 |
| 2008/0011336 A1 | 1/2008 | Hamaguchi |

FOREIGN PATENT DOCUMENTS

| DE | 20117255 | 5/2002 |
| DE | 20305443 | 6/2003 |
| EP | 1811471 | 7/2007 |
| GB | 2232902 | 1/1991 |
| JP | 58112055 | 7/1983 |
| JP | 2004281250 | 10/2004 |
| JP | 2005168648 | 6/2005 |
| JP | 2009072746 | 4/2009 |
| WO | WO0107890 | 2/2001 |

* cited by examiner

Primary Examiner — Edward Wojciechowicz
(74) Attorney, Agent, or Firm — Saliwanchik, Lloyd & Eisenschenk

(57) ABSTRACT

A device for tempering a test fluid includes an electric heating device for heating the test fluid, a sensor for detecting a measuring value associated with the temperature of the test fluid, and an electronic control device for controlling the heating device in dependence upon the measuring value. The heating device includes an induction generator, connected to a power supply, for the inductive heating of a heating element which is connected, in a heat-conducting manner, to the test fluid and/or to a container for the test fluid, and the sensor is a sensor measuring in a contact-less manner.

23 Claims, 3 Drawing Sheets

DEVICE FOR TEMPERING A TEST FLUID

BACKGROUND OF THE INVENTION

1. Field of the Invention

The invention relates to a device for tempering a test fluid.

2. Description of the Background of the Invention

Test devices are used for example in the pharmaceutical industry to test the disintegration or dissolution of pharmaceutical substances in a test fluid, see for example DE 203 05 443 U1, DE 201 17 255 U1, U.S. Pat. No. 6,484,595. In conventional test devices, a beaker filled with test fluid is kept in a water bath which is kept at the desired test temperature by means of a heating element and a feedback control, see for example DE 83 36 233 U1 and DE 38 04 688 A1. However, the use of a water bath has a series of disadvantages. It takes a long time for the water bath to be heated to the desired test temperature. The temperature control has a considerable time lag which means that during testing deviations from the desired temperature can occur. Furthermore, for hygiene reasons, regular laborious emptying, cleaning and re-filling of the water bath are necessary. Finally, the temperature of the test fluid can be determined during testing only indirectly by measuring the temperature of the water bath which results in a systematic measuring inaccuracy.

DE 35 20 034 C1, EP 0 746 750 B1 and DE 199 23 918 A1 disclose devices in which heating is effected by means of a heating sleeve surrounding the container for the test fluid, whereby there is no need to provide a water bath. However, this type of heating also has a significant time lag owing to the necessary heat transfer through the container which generally consists of glass. In addition, the heating sleeve has a negative effect on the ability to inspect the test fluid.

DE 201 17 255 U1 discloses a device for controlling the temperature of a test fluid having a metallic pot which can be heated by means of a heating plate and is to be filled with water and into which the container for the test fluid can be inserted, wherein evaporation of the water from the metallic pot is counteracted by means of a sealing sleeve. This construction is comparatively complicated and is additionally prone to errors since it is easy to forget to fill the metallic pot with water, which is required for effective heat contact. Also, owing to the transfer of the thermal heat through the metallic pot and through the wall of the test fluid container, the feedback control is comparatively slow. Finally, owing to the arrangement of the temperature sensor in the region of the heating plate, the measured temperature does not correspond to the temperature of the test fluid.

WO 01 07890 A2 discloses in one embodiment a microtitre plate having depressions which include a metal piece loosely placed on the base of the depression. An induction coil is disposed beneath the microtitre plate for the inductive heating of the metal piece. The heating of the water in the depressions is controlled by means of a temperature control unit.

GB 2 232 902 A discloses a device for separating and measuring the liquid and solid phases of drill samples. In one embodiment, the drill sample is placed into a distillation vessel consisting of steel. Induction flows are produced in the walls of the distillation vessel by means of an induction coil disposed around the distillation vessel and this vessel is consequently heated in order to distil off the liquid components. The heating of the distillation vessel is thermostatically controlled to a temperature of 500° C.±38° C. by means of a temperature sensor disposed in contact with the base of the distillation vessel.

JP 58 112055 A describes a transparent container consisting of glass or a synthetic material for heating a fluid, wherein a magnetic body, which produces heat by means of high-frequency induction, is incorporated in the wall of the container.

U.S. Pat. No. 5,232,667 discloses a temperature control system having a resistive heating element for a sample insert in an electrochemical diagnosis system for biological samples. EP 1 811 471 A1 relates to an inductive heating unit for preserved foodstuffs in a vending machine. US 2008 0011336 A1 discloses an induction device for heating clean water flowing through a pipe. JP 2009 072746 A discloses a stirring device having an impellor, which can be inductively heated and consists of steel, and a temperature control function. JP 2005 168648 A discloses a cooking vessel which can be inductively heated. JP 2004 281250 A discloses a temperature control unit for an inductive heating device for heating a fluid stored in a tank.

SUMMARY OF THE INVENTION

It is an object of the invention to provide a device in which rapid heating of the test fluid and rapid and accurate control of the test temperature are achieved with as small time lag as possible.

The invention achieves this object by means of the features of the independent claims. Owing to the direct and rapid inductive heating, there is no need to provide a water bath for heating the test fluid and all of the disadvantages associated therewith can be obviated.

The inductive heating in accordance with the invention is provided by the preferred arrangement of the heating element on or in a removable container for the test fluid, whereby there is no need to provide disruptive connecting lines for the power supply to the heating element. This arrangement of the heating element contributes to a more direct and more rapid heat transfer from the heating element to the test fluid. The arrangement of the heating element in the test fluid container in direct contact with the test fluid is further preferred, whereby a direct heat transfer from the heating element to the test fluid and a temperature control with minimum time lag are permitted. This can be achieved in a particularly simple manner by a separate heating element which can be placed in the test fluid container, which permits the use of current test fluid containers. However, the invention also covers the mounting of the heating element on a surface of the container or within a container wall. In some circumstances, it may be preferred to arrange the heating element so it is not in direct contact with the test fluid, in particular on the exterior of the container or within a container wall, e.g., when test conditions stipulate that the heating element cannot be in direct contact with the test fluid.

In accordance with the invention, the sensor for detecting a measuring value related to the temperature of the test fluid is a sensor which measures in a contact-less manner, in particular by means of electromagnetic radiation. Accordingly, the sensor is disposed in an expedient manner so that it does not contact the test fluid nor a container for the test fluid such that the measuring path between the sensor and the test fluid is substantially radiation-transparent in relation to the radiation used for measuring purposes. In particular, in an expedient manner, any walls, sensor covers or other devices which are disposed between the sensor and the test fluid are designed to be radiation-transparent at least in this respect or comprise corresponding through-going apertures for the measuring radiation. Preferably only the wall of the container for the test fluid is disposed between the sensor and the test fluid. For example, when measuring from the top, the measuring path between the sensor and the test fluid can also be free. Owing to the contact-less sensor arrangement, a direct, time lag-free measurement of the temperature of the test fluid is possible. A complicated and error-prone immersion of a temperature sensor into the test fluid and disruptive external signal lines for the sensor are obviated.

A preferred application of the invention relates to test devices for testing the disintegration or dissolution of a substance introduced into the test fluid. Such test devices are used for example in the pharmaceutical industry for testing the disintegration or dissolution of pharmaceutical substances in a test fluid. Applications in test devices outside the pharmaceutical industry, e.g., in the food or cosmetics industry as well as in medical engineering, are also feasible.

BRIEF DESCRIPTION OF THE DRAWINGS

The invention is described hereinafter with the aid of advantageous embodiments with reference to the attached Figures, in which.

DETAILED DESCRIPTION OF THE DRAWINGS

Figure 1:
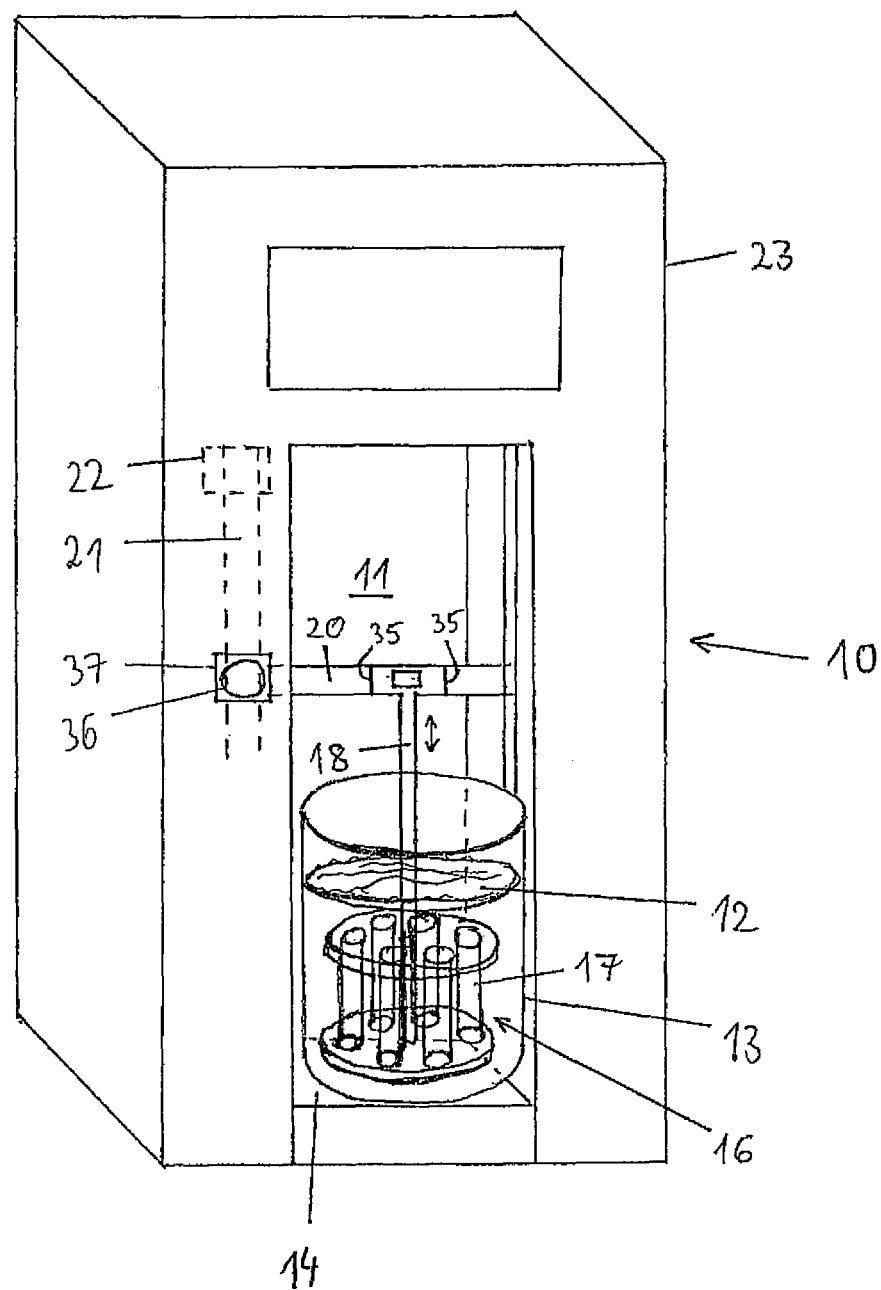
FIG. 1 shows a perspective view of the front side of a device for testing the disintegration time of tablets.
Figure 2:
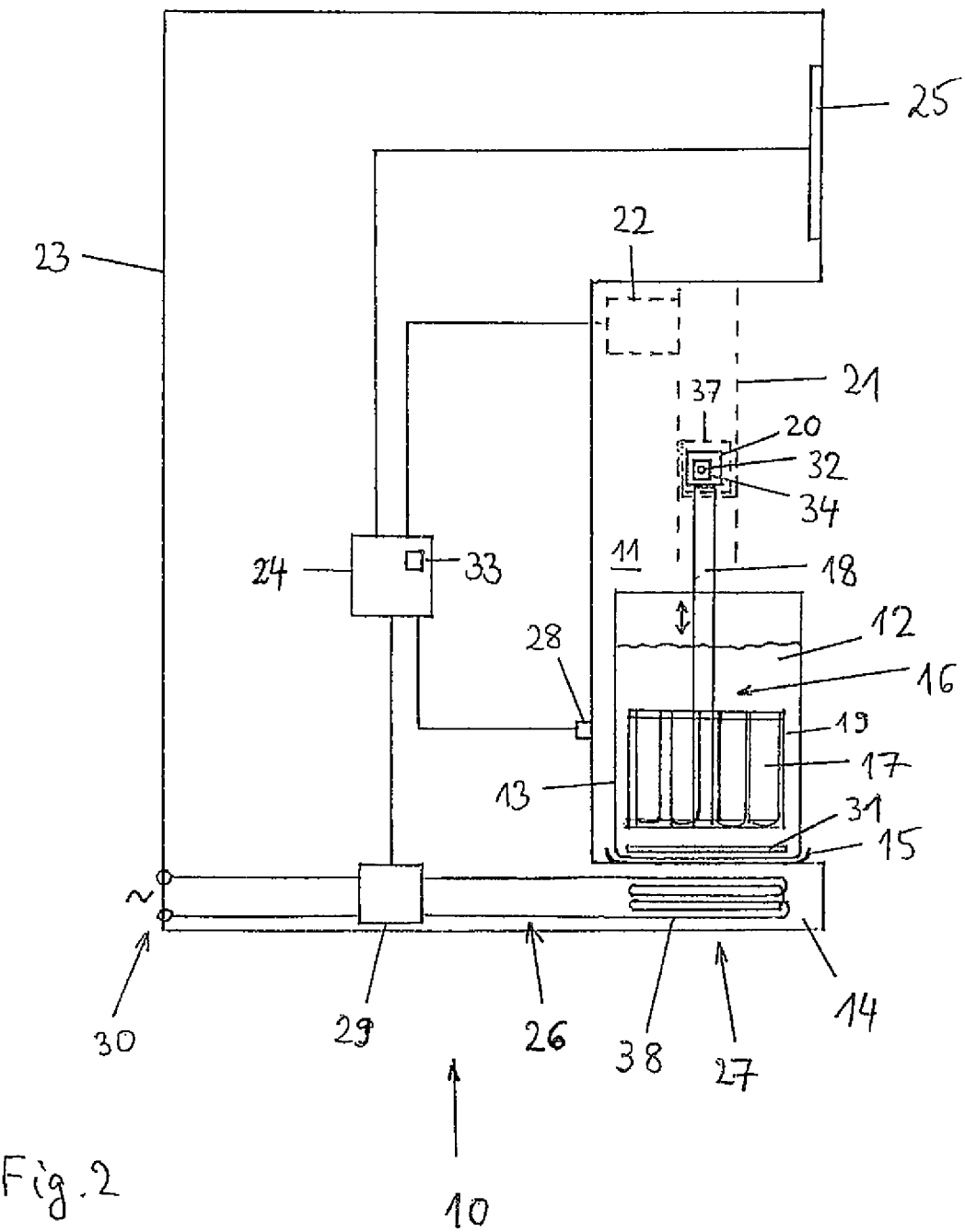
FIG. 2 shows a schematic cross-sectional view of the test device of FIG. 1.

The device 10 for testing the disintegration time of tablets, pills, lozenges or the like includes a housing 23, which forms a bearing base 14 for a beaker-shaped container 13 containing a test fluid 12, and a cage unit 16 having a frame 19 which is arranged to receive e.g., six test tubes 17 which are open at the top and into which the tablets to be tested are inserted. The cage unit 16 includes a shaft 18 which extends from the top into the container 13 and on the lower end of which the frame 19 is attached and which is arranged to be attached at its upper end to an in particular bracket-shaped support 20. The support 20 can be reciprocally adjusted vertically in the test device 10 by means of a linear guide 21 having an in particular electric drive 22 in order to subject the frame 19 to a periodic lifting and lowering movement in the test fluid 12 during the test process, as shown in FIGS. 1 and 2 by means of the double arrow. The housing 23 preferably forms a receiving chamber 11 for the beaker-shaped container 13.

An electronic control unit 24 is disposed in the housing 23 and is arranged or programmed to automatically control a test process in the test device 10 by means of software stored therein and expediently comprises a microprocessor or microcontroller. The electronic control unit 24 is for this purpose connected to the components of the test device 10 which are to be controlled and emit signals, e.g., the drive 22 and a display and/or operating device 25 for displaying user information. The display/operating device 25 is preferably a touch-screen in order to provide the operator with a user-friendly input means, e.g., in order to start the implementation of a test process. There is then no need to provide separate input means such as push buttons etc.

During the entire testing of the disintegration time of tablets, the temperature of the test fluid 12 is to be kept within a predetermined range, in particular a range of a few ° C., e.g., plus/minus 2° C., about an average normal human body temperature of for example 37° C. For this purpose, the test device 10 includes a temperature feedback control circuit 26 having a heating device 27 for heating the test fluid in dependence upon a temperature measuring value, measured by means of a temperature sensor 28, as a feedback control variable, wherein the feedback control is effected in the electronic control device 24. The operator can set via the display and operating device 25 the test process to start automatically as soon as the test fluid has reached the desired temperature.

The heating device 27 includes an electrical induction generator which is preferably disposed in the base 14 of the test device 10 and is in the form of a preferably planar coil 38 which can be connected to a power source 30, in particular alternating current supply, via a switching device 29 which can be switched by the control unit 24. The heating device 27 further includes an induction receiver 31 in which an electrical current flow is produced when there is a current flow through the induction generator 38 owing to electromagnetic induction, whereby the induction receiver 31 acts as a heating element.

In the preferred embodiment in accordance with FIGS. 1 and 2, the heating element 31 is a separate part which is expediently metallic and is simply placed in the beaker-shaped container 13 and has no direct connection to the device 10. The heating element 31 is in direct contact with the test fluid 12, whereby time lags during temperature control are minimised. Owing to the wirelessly acting induction principle, disruptive supply lines between the heating element 31 and the device 10 can be obviated.

The heating element 31 is preferably formed so as to be flat in order that container 13 of a conventional constructional height can be used. The thickness of the heating element 31 is preferably at most 10 mm, more preferably at most 5 mm, for example approximately 1 or 2 mm. A particularly simple and thus preferred embodiment of the heating element 31 is a plate, however the heating element 31 can also have any other suitable shape, e.g., it can be formed as a ring, grid or the like. The diameter of the heating element 31 is preferably adapted to the inner diameter of the beaker-shaped container 13 in the base region in order to ensure that the heating element 31 is centrally aligned in the container 13.

The contact-less temperature sensor 28 which is disposed in a surface of the housing 23 facing the container 13 and is sensitive to electromagnetic radiation is preferably based on a measurement of the heat radiation emitted by the test fluid 12. The temperature sensor 28 is preferably an infrared sensor. The temperature sensor 28 is disposed so as to be spaced apart from the container 13 and also from the test fluid 12. Only the radiation-transparent wall of the container 13 is disposed between the temperature sensor 28 and the test fluid 12. Owing to this contact-less arrangement, there is no need to provide an external temperature sensor having disruptive external signal lines. In addition, the infrared sensor 28 permits the direct detection of the temperature of the test fluid 12 and not simply an indirect measurement by detecting the temperature of a component heated by the test fluid 12.

The temperature sensor 28 is preferably disposed so as to be spaced apart, in particular vertically above, from the heated element 31 so that the temperature measurement is as far as possible not influenced by the heat radiation emitted by the heating element 31. The temperature sensor 28 is preferably disposed at least 10%, more preferably at least 20%, still more preferably at least 30%, for example in the range of 40% to 60%, with respect to the height of the beaker-shaped container 13, above the heating element 31 or above the base of the container 13. Measuring from the top is also possible.

The disintegration time of a tablet is measured in a known manner, e.g., by means of a body placed into the test tube 17, which body puts a load on the tablet and, owing to the disintegration of the tablet, comes to rest against the base of the test tube 17 and closes a contact. In order to transmit a signal measuring the disintegration time from the cage unit 16 to the control unit 24, the test device 10 preferably comprises a wireless transmission device having a radio transmitter 32 attached to the cage unit 16 and a radio receiver 33 which is connected to the control unit 24 and is preferably part thereof. In order to process the measuring and control signals, the cage unit 16 preferably includes a dedicated electronic control device 34 having a microprocessor or microcontroller. The radio transmitter 32 and radio receiver 33 are preferably both formed as a sending/receiving unit in order to enable the transmission of control signals from the control unit 24 to the control device 34, thus enabling bidirectional communication. The radio transmitter 32 can be part of the control device 34.

The cage unit 16 includes connection means 35 for releasably connecting the cage unit 16 to the support 20. Owing to the wireless inductive heating of the heating element 31, the wireless radio transmission between the control devices 24 and 34 and the contact-less temperature measurement by means of the IR temperature sensor 28, the container 13 with the fitted cage unit 16 can be placed onto the base 14 as a whole unit by the operator prior to a test procedure and the cage unit 16 can be suspended in the support 20, and after a test procedure has finished, the cage unit 16 can be detached from the support 20, and the container 13 with the cage unit 16 can be removed, wherein the time-consuming connection/disconnection of signal or supply lines or further measures such as the insertion of a temperature sensor into the container 13 are completely omitted.

In order to prevent the drive 22, which is preferably designed as a stepping motor or brushless DC motor, from moving during the suspension of the cage unit 16 in the support 20 or during its detachment therefrom, the support 20 is preferably mechanically decoupled from the linear guide 21 by means of one or more permanent magnets 36 and a ferromagnetic part 37 co-operating therewith.

With regard to the container 13 being centrally aligned relative to the test device 10, the bearing base 14 preferably comprises means for positioning the container 13 on the bearing base 14, e.g., a circumferential collar 15 as shown in FIG. 2.

The test device 10 preferably includes means for detecting a change in inductance of the induction generator 38. These means can be formed for example by a suitable circuit in the switching device 29. Since placing or removing the container changes the inductance of the coil 38 owing to the heating element 31, it can thus be determined by means of a corresponding measurement whether or not the container 13 is disposed on the base 14 in a manner suitable for operation. The control unit 24 can display the determined condition to the operator by means of the display device 25. Furthermore, the sequence control can be effected in dependence upon the determined condition; for example, provision can be made that current flow through the induction generator 38 only occurs when the container 13 is disposed on the base 14 in a manner suitable for operation.

The test fluid 12 can be for example water, artificial gastric juice or chyle depending upon the test application. The beaker-shaped container 13 and the test tubes 17 preferably consist of transparent material, e.g., glass or a transparent synthetic material, in order to ensure that the test process can be inspected e.g., via video recording.

The test device 10 can include electronic storage means to store a series of temperature measuring values measured over a test time period, in order to enable complete documentation of the test process. The storage means can be formed in the control unit 24.

The invention can also be applied to other test devices. For example, test devices for testing the dissolution of a pharmaceutical substance in a test fluid are known, wherein instead of a cage unit which is periodically reciprocally moved in the test fluid, a stirring rod is provided for continually circulating the test fluid. Systems with a plurality of test containers can also be constructed in accordance with the invention, in that dedicated inductive heating and a dedicated temperature sensor having a corresponding temperature control circuit are provided for each test container.

Figure 3:
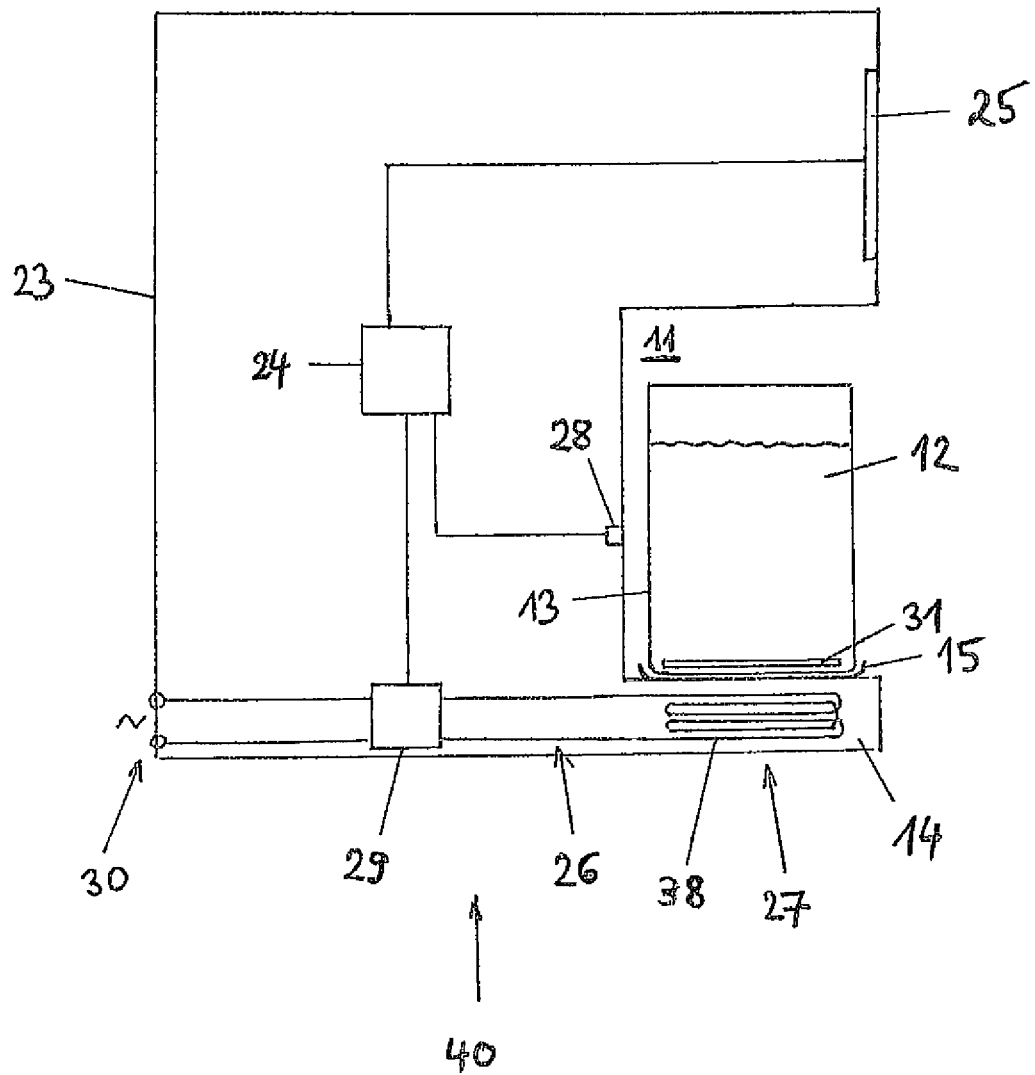
FIG. 3 shows a schematic cross-sectional view of a pre-heating device.

Finally, the invention is not limited to test devices. The exemplified embodiment in accordance with FIG. 3 shows for example a preheating station 40 which is arranged to preheat a test fluid 12 in a container 13 to a desired temperature for its subsequent use and to keep it at this temperature. Such preheating stations 40 are used for example in conjunction with a test device 10 in order to be able to immediately start testing after the test fluid container 13 has been changed, which enables the overall test duration to be considerably reduced.

The preheating station 40 can be formed substantially identical to the test device 10, but without a cage unit 16 and the devices associated therewith. Of course, the display and operating unit 25 for the preheating station 40 for example can be omitted if need be.

In the illustrated embodiments, the heating device 27 is disposed in an advantageous manner in the region of the base of the container 13. However, this is not absolutely necessary. For example, the heating element 31 can be a plate which is hung on the inside or outside on a lateral wall of the container 13 and is heated by a laterally disposed coil 38.

I claim:

1. An apparatus for heating a test fluid, comprising:
a housing, wherein the housing is adapted to removably receive a container;
an inductive heating device, wherein the inductive heating device comprises an induction generator located within the housing and a heating element, wherein the induction generator is adapted to inductively heat the heating element;
an infrared sensor for detecting a temperature of a test fluid positioned in the container, wherein the infrared sensor directly detects the temperature of the test fluid; and
and an electronic control device, wherein the electronic control device controls the inductive heating device based on the measuring value, wherein when the induction generator inductively heats the heating element and the heating element is in thermal contact with the test fluid, the test fluid is heated.

2. The apparatus according to claim 1, wherein the apparatus further comprises a base, wherein the base is adapted for the container to be positioned on the base.

3. The apparatus according to claim 1, wherein the heating element is adapted for arrangement on or in the container such that the heating element is in thermal contact with the test fluid.

4. The apparatus according to claim 1, wherein the heating element is a separate part adapted for insertion directly into the test fluid.

5. The apparatus according to claim 1, wherein the infrared sensor is positioned above the heating element.

6. The apparatus according to claim 1, wherein the infrared sensor is sensitive to electromagnetic heat radiation emitted from the test fluid.

7. The apparatus according to claim 1, further comprising a circuit for detecting a change in inductance of the induction generator.

8. The apparatus according to claim 1, further comprising a sample unit for receiving a substance to be tested, wherein the sample unit is adapted to be positioned such that the substance is in the test fluid.

9. The apparatus according to claim 8, wherein a signal is generated when the substance disintegrates or dissolves.

10. The apparatus according to claim 9, further comprising a drive device for periodically moving the sample unit in the test fluid.

11. The apparatus according to claim 9, further comprising a cable-less transmission device for transmitting data between the sample unit and the electronic control device.

12. The apparatus according to claim 9, wherein the sample unit comprises a sample unit electronic control device.

13. The apparatus according to claim 9, further comprising a support for the sample unit, wherein the sample unit is suspended magnetically from the support.

14. The apparatus according to claim 1, wherein the heating element is formed so as to be substantially flat.

15. The apparatus according to claim 1, wherein the apparatus further comprises a container, wherein the container comprises a wall that is transparent to infrared radiation, wherein the infrared sensor directly detects the temperature of the test fluid through the wall when the container is received in the housing and the test fluid is in the container.

16. The apparatus according to claim 1, wherein the infrared sensor detects the temperature of the test fluid through an opening in the container when the container is received by the housing and the test fluid is in the container.

17. The apparatus according to claim 1, wherein the infrared sensor detects the temperature of the test fluid through a wall of the container that is transparent to infrared.

18. The apparatus according to claim 1, wherein the electronic control device maintains the temperature of the test fluid within a desired temperature range of a desired temperature.

19. The apparatus according to claim 17, wherein the desired temperature range is the desired temperature minus 2° C. to the desired temperature plus 2° C.

20. The apparatus according to claim 17, wherein the desired temperature is 37° C.

21. The apparatus according to claim 17, wherein the desired temperature is above an average minimal human body temperature.

22. The apparatus according to claim 1, wherein the induction generator is disposed in the base.

23. The apparatus according to claim 1, wherein the infrared sensor is located within the housing.

* * * * *